United States Patent [19]

Bar-Shalom

[11] Patent Number: 4,665,063

[45] Date of Patent: May 12, 1987

[54] METHOD OF TREATING ACNE

[75] Inventor: Daniel Bar-Shalom, Haifa, Israel

[73] Assignee: Rafa Laboratories Ltd., Israel

[21] Appl. No.: 754,438

[22] Filed: Jul. 12, 1985

[30] Foreign Application Priority Data

Jun. 13, 1983 [IL] Israel ......................................... 68965

[51] Int. Cl.⁴ ........................................... A61K 31/605
[52] U.S. Cl. .................................... 514/164; 514/165;
514/859
[58] Field of Search ................................ 514/165, 164

[56] References Cited

U.S. PATENT DOCUMENTS 4,219,548 8/1980 Reller .................................... 424/234
4,364,940 12/1982 Neiss et al. .

OTHER PUBLICATIONS

Chemical Abstracts 77: 105596s, 1977 (Broutin et al.).
Chemical Abstracts 92: 116448j, 1980 (Schweckendiek).
Merck Index, 9th ed., 1976, paragraph 847.

*Primary Examiner*—Leonard Schenkman

[57] ABSTRACT

The present invention relates to a composition and to a method for the treatment of dermatological disorders such as acne, by topically applying acetyl salicyclic acid within a carrier.

2 Claims, No Drawings

METHOD OF TREATING ACNE

CROSS-REFERENCE TO RELATED APPLICATIONS

The present application is a continuation-in-part of co-pending U.S. patent application Ser. No. 598,572, filed Apr. 9, 1984 now abandoned.

BACKGROUND OF THE INVENTION

The present invention relates to a pharmaceutical preparation for topical administration in the treatment of various dermatological disorders, e.g. psoriasis, acne, seborrheic dermatitis, idiopathis vitiligo and bullous pemphigoid, comprising acetyl salicylic acid as the active ingredient. The present invention is also directed to a method for treating these various dermatological disorders, which comprises administering a composition having acetyl salicylic acid as the active ingredient.

Acetyl salicylic acid has been well known as a therapeutically active compound. It is known as a very effective analgesic, antipyretic and anti-inflammatory agent. Thus far, acetyl salicylic acid has been orally administered, i.e. in the form of a tablet, capsule, etc., or has been administered by injection.

Numerous experiments have been conducted for administering acetyl salicylic acid not in the form of tablets, but in a more pleasant form. Israeli patent specification No. 44,774 discloses a pharmaceutical composition which is to be orally administered after having been dissolved in water. The aqueous solution has to be quickly administered, otherwise the acetyl salicylic acid will become hydrolyzed. Moreover, such an aqueous solution certainly cannot be stored for an extended period of time.

A stable liquid acetyl salicylic acid composition which is also orally administered, is disclosed in Israeli patent specification No. 44,485. An advantage of this solution is that it results in a more palatable form of administration, which is important in pediatric practice. However, external utilization of this composition has not been considered.

Experiments in which compositions were prepared enabling the external use of acetyl salicylic acid in the treatment of certain diseases, are known from Psoriasis, Proceedings of the Second International Symposium, 1976. The concentration of the acetyl salicylic acid in these compositions was 1-2% (all percentages listed in the present application are percentages by weight). However, the authors of this publication specifically stated that these compositions were not effective against psoriasis.

The inhibitory effect of certain compounds, inter alia, acetyl salicylic acid, on the development of erythema in guinea pigs, was tested by Erich C. Weirich et al., Dermatology 152, 87-99 (1976). The concentrations of these compounds, i.e. of acetyl salicylic acid in the tested compositions, was 0.05-5%. A certain external anti-inflammatory effect was observed for acetyl salicylic acid. However, this effect was not sufficient, and in particular, it did not give any hint that acetyl salicylic acid in a concentration of at least 11% is very effective in the treatment of dermatological disorders, in particular acne.

SUMMARY OF THE INVENTION

Accordingly, it is an object of the present invention to improve the treatment of dermatological disorders.

It is also an object of the present invention to improve the particular treatment of acne.

It is another object of the present invention to improve treatment of various lesions which typify acne.

These and other objects are provided by the present invention which is directed to a pharmaceutical preparation for topical administration in the treatment of dermatological disorders, which comprises acetyl salicylic acid as the active ingredient, together with a suitable carrier. More particularly, the present invention is especially directed to a composition for the treatment of acne, this composition consisting of a solution of acetyl salicylic acid dissolved in ethanol, in an amount of 11% by weight to saturation. The saturation level of the acetyl salicylic acid in the ethanol is generally about 12.5–13% by weight.

The present invention is also directed to a method for the treatment of dermatological disorders, by topically applying to the situs of such disorders, acetyl salicylic acid as the active ingredient, together with a suitable carrier. More particularly, the present invention is directed to a method for the treatment of acne, by topically applying to the situs of such a dermatological disorder, a solution of acetyl salicylic acid dissolved in ethanol, in an amount of 11% by weight to saturation (about 12.5 to 13% by weight).

The preparation of the present invention may have any suitable form, e.g. an ointment, solution, emulsion, lotion, etc. While physiologically acceptable and compatible carriers for the acetyl salicylic acid include liquid paraffin, lanolin, white soft paraffin, white bees wax, hard paraffin, and certain alcohols such as propanol, isopropyl alcohol, glycerol and glycol, along with mixtures of any thereof, the especially-preferred carrier for the acetyl salicylic acid is ethanol alone, with the acetyl salicylic acid being present in the ethanol in the amount of 11% by weight to saturation. In this regard, the concentration of the acetyl salicylic acid within the ethanol may vary to a certain degree. However, it has been found that the preferred concentration is about 11% by weight to saturation, most preferably about 12.5 to 13% by weight (about the level of saturation of acetyl salicylic acid in ethanol).

As noted above, the present invention is also directed to a method for the treatment of dermatological disorders, comprising administering a preparation as defined above in pre-determined doses at pre-determined intervals. The doses administered are preferably 7-15 mg/mm of skin, with the intervals between each dose preferably being about 24 hours, until the lesions disappear.

The composition and method of the present invention are suitable for the treatment of various dermatological disorders such as psoriasis, idiopathic vitiligo, seborrheic dermatititis and bullous pemphigoid, especially for the treatment of acne. As described in Dermatology, Third Edition, the C.V. Mosby Company, St. Louis (1974), in Chapter 6, notably at page 91, the clinical lesions which typify acne include comedones, papules, pustules, cysts, and scars. The preferred embodiments of the present invention, i.e. where acetyl salicylic acid is present in just the ethanol carrier alone, in the amount of 11% by weight to saturation, are especially effective for treating the comedones, papules, pustules which typify the dermatological disorder of acne.

DESCRIPTION OF THE PREFERRED EMBODIMENTS

The present invention will be further described in greater detail, with reference to the following examples to which the present invention is not to be restricted. In all the following examples, the preparations were prepared by suitable pharmaceutical methods, i.e. by way of admixing the separate ingredients until a homogeneous preparation was obtained.

EXAMPLE I

An ointment comprising the following ingredients was prepared:

| INGREDIENT | AMOUNT |
| --- | --- |
| Acetyl salicylic acid | 12.5 g |
| White bees wax | 1.75 g |
| Hard paraffin | 7.0 g |
| White soft paraffin | up to 100.0 g |

Seven individuals suffering from psoriatic skin were treated with the above ointment. The ointment was smeared on discrete marked areas twice daily for at least two weeks. In six of the cases, complete healing was achieved within 7-11 days, while there was a slight improvement in the remaining case.

EXAMPLE II

An ointment comprising the following ingredients was prepared:

| INGREDIENT | AMOUNT |
| --- | --- |
| Acetyl salicylic acid | 10.0 g |
| 10% Lanolin in soft white paraffin | up to 100.0 g |

The preparation was applied to the psoriatic skin of 15 individuals, using different criteria for control (for example, the ointment was applied over a limited area within a lesion which was ultimately compared with the remainder of the lesion, or the ointment was applied over one limb which was ultimately compared with a second untreated limb, etc.). There was a noticeable improvement in 13 of the cases, with very slight improvement in one of the cases, and no change in another of the cases.

While the average time for complete clearing of the lesion was 8 days, there was a remarkable case of a young girl whose ears were completely cleared within 48 hours.

EXAMPLE III

A lotion comprising the following ingredients was prepared:

| INGREDIENT | AMOUNT |
| --- | --- |
| Acetyl salicylic acid | 10 g |
| Propylene Glycol | up to 100 g |

The lotion was rubbed each day on the scalp of 8 psoriatic individuals. There was a tremendous improvement in all cases. In six of the cases, the scales disappeared completely after treatment for two weeks.

EXAMPLE IV

An ointment comprising the following ingredients was prepared:

| INGREDIENT | AMOUNT |
| --- | --- |
| Acetyl salicylic acid | 10 g |
| Lanoline | 9 g |
| Soft white paraffin | 81 g |

Fifty patients suffering from psoriatic lesions were treated with this ointment. These patients had plaques of medium size which were distributed over the arms, legs, or body (particularly in the region of the neck). All the lesions were treated with ointment for about 2 weeks. Complete healing was observed in 50% of the cases, while those patients with extremely large lesions reported a great improvement, but not complete healing. It was noted that lesions in the area of the head and neck cleared more rapidly than lesions on the arms, while lesions on the legs cleared more slowly. Of the 50 treated cases, two did not respond to treatment. In one case, the patient discontinued the therapy after two treatments (no explanation was given).

Three of the treated patients suffered from diabetes, and were unable to use corticosteroids. These three patients reported marked improvement following application of the ointment for about two weeks, however the rate of improvement was slower as compared with the non-diabetic patients.

EXAMPLE V

A lotion of 11% acetyl salicylic acid in ethanol was prepared. Eighty patients suffering from acne were treated with this lotion. No new lesions or pustules appeared following several days of treatment, and the acne rapidly cleared. All patients were instructed to discontinue other forms of acne treatment, and to use only the lotion once a day, with clearing being observed within two days. One female patient, aged 28, who had complained of severe outbreaks of acne coinciding with menstruation, reported that treatment with the lotion cleared up her acne completely within a few days.

EXAMPLE VI

Four cases of previously-diagnosed idiophatic vitiligio were treated with the ointment described in Example IV. Complete healing, i.e. repigmentation of the area of the skin, was observed in all four cases following treatment extending over a period of 6 to 12 weeks.

EXAMPLE VII

A lotion comprising the following ingredients was prepared:

| INGREDIENT | AMOUNT |
| --- | --- |
| Acetyl salicylic acid | 8 g |
| 50:50 Propylene glycol/Isopropyl alcohol | 92 g |

This lotion was tried on patients, in particular young children aged 3 to 5 years suffering from seborrheic dermatitis and was found to be effective.

EXAMPLE VIII

A female, aged 80 years, with an eruption which had been diagnosed as bullous pemphigoid was treated with the ointment described in Example IV for three weeks. The bullae disappeared completely, and no recurrence was reported.

EXAMPLE IX

An albino individual, who was unable to tolerate exposure to sunlight, was treated with the ointment described in Example IV which was applied to the face of the individual. The application prevented erythema which is caused by exposure to radiant heat.

EXAMPLE X

One hundred eighty four patients who were suffering from various lesions typifying acne, were treated with a saturated solution of acetyl salicylic acid in ethanol. The following results were observed:

| Time of Observation | PATIENTS SUFFERING FROM | | |
|---|---|---|---|
| | Comedones | Papules | Pustules |
| After 2 weeks of Treatment | +(Probably old) | — | 12 |
| After 1 Month of Treatment | 9 | — | — |

90 patients suffering from various lesions constituting acne, were treated with a 10% solution of acetyl salicylic acid in ethanol. The following results were observed:

| Time of Observation | PATIENTS SUFFERING FROM | | |
|---|---|---|---|
| | Comedones | Papules | Pustules |
| After 2 weeks of Treatment | + | 18 | 21 |
| After 1 month of Treatment | — | 6 | 11 |

27 female patients, ages 13-17 when the problem of pustules is most acute, were treated with a saturated solution of acetyl salicylic acid in ethanol, within two years from the first menstruation thereof. The results were observed as follows:

| Time of Observation | PATIENTS SUFFERING FROM Pustules |
|---|---|
| After 2 weeks of Treatment | 3 |
| After 1 month of Treatment | — |

30 similar female patients were treated with a 10% solution of acetyl salicylic acid in ethanol. The observed results were as follows:

| Time of Observation | Patients Suffering from Pustules |
|---|---|
| After 2 weeks of Treatment | 21 |
| After 1 month of Treatment | 14 |

The preceding description of the present invention is merely exemplary, and is not intended to limit the scope thereof in any way.

What is claimed is:

1. Method for the treatment of the dermatological disorder of acne, which comprises
    topically applying to the situs of such dermatological disorder, a composition consisting of a solution of 12.5 to 13% by weight of acetyl salicylic acid dissolved in ethanol.
2. The method of claim 1, which comprises applying said acetyl salicylic acid in said ethanol, in doses of 7-15 mg/mm of skin over intervals of about 24 hours between respective doses.

* * * * *